US00PP17293P2

(12) United States Plant Patent
Eggleton

(10) Patent No.: US PP17,293 P2
(45) Date of Patent: Dec. 19, 2006

(54) ***GAURA* PLANT NAMED 'SME-2'**

(50) Latin Name: *Gaura lindheimeri*
Varietal Denomination: SME-2

(76) Inventor: Steven Eggleton, Plant Growers Australia, 3 Harris Rd, Wongapark, Vic (AU), 3115

( * ) Notice: Subject to any disclaimer, the term of this patent is extended or adjusted under 35 U.S.C. 154(b) by 54 days.

(21) Appl. No.: 11/100,085

(22) Filed: Apr. 5, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

2006/0095995 P1 * 5/2006 Kataoka ..... Plt./263

* cited by examiner

*Primary Examiner*—Wendy Haas

(57) ABSTRACT

A new cultivar of *Gaura* plant named 'SME-2' characterized by dense, upright habit, green and purple-red foliage, purple-red flower stalks and rose-pink flowers. In combination these traits set 'SME-2' apart from all other existing varieties of *Gaura* known to the inventor.

3 Drawing Sheets

Genus: *Gaura.*
Species: *lindheimeri.*
Denomination: 'SME-2'.

BACKGROUND OF THE INVENTION

The present invention relates to a new and distinct variety of *Gaura* grown for use as an ornamental plant for the landscape. The new cultivar is known botanically as *Gaura lindheimeri* and will be referred to hereinafter by the cultivar name 'SME-2'.

'SME-2' is a hybrid plant that arose in a cultivated area in Wonga Park, Victoria, Australia, as follows:

In the spring of 2002, the inventor discovered growing in a bed of plants of *Gaura lindheimeri* 'Passionate Pink' (unpatented) a single plant which exhibited a denser habit than *Gaura lindheimeri* 'Passionate Pink'. This discovery was of interest to the inventor since, although *Gaura lindheimeri* 'Passionate Pink' is very quick to grow and flower, it soon develops a lax or open habit. The discovery is presumed to be a chance seedling which resulted from the open pollination of plants of the surrounding plants of *Gaura lindheimeri* 'Passionate Pink'. Plants of the species *Gaura lindheimeri* have a tendency to self-seed if numerous flower stems are left in place. However, most cultivars of *Gaura lindheimeri,* including *Gaura lindheimeri* 'Dauphine' (unpatented)—which was the pollen parent of *Gaura lindheimeri* 'Passionate Pink'—appear to be sterile.

The inventor marked the single discovered plant and allowed it to run to seed so that further plants could be raised from this improved selection. The seed was collected and sown immediately. In summer 2002/2003, the resulting seedlings were transplanted into individual 14 cm diameter containers which were planting out into a trial bed for over-wintering and evaluation as freshly-grown plants in spring 2003. After repeated observation of the trials plants during spring and summer 2003, the inventor selected and removed for asexual reproduction and further trials a single plant to be known as 'SME-2'. The inventor selected 'SME-2' for its particular combination of overall plant size and form which is dense and upright, its foliage which is both green and purple-red, its purple-red flower stalks, and its rose-pink flowers.

'SME-2' was first asexually propagated by the inventor in 2003 from vegetative (non-flowering) stem cuttings taken from the original plant 'SME-2'. The cuttings were grown to rooted plug stage and then transferred to 140 mm. containers, filled with pine bark based mix containing controlled release fertilizer. The resulting plants were determined to exhibit the same characteristics as the originally selected plant 'SME-2' and from subsequent asexual reproductions the inventor has determined that the new variety 'SME-2' is stable and reproduces true to type.

When compared with *Gaura lindheimeri* 'Passionate Pink', 'SME-2' is readily distinguished by its dense foliage habit, whereas *Gaura lindheimeri* 'Passionate Pink' exhibits a somewhat sparse growth habit.

SUMMARY OF THE INVENTION

The following traits have been repeatedly observed and represent the distinguishing characteristics of the new plant 'SME-2'. In combination these traits set 'SME-2' apart from all other *Gaura* known to the inventor. 'SME-2' has not been tested under all possible conditions and phenotypic differences may be observed with variations in environmental, climatic and cultural conditions, however, without any variance in genotype.

1. *Gaura* 'SME-2' exhibits a dense, upright habit.
2. *Gaura* 'SME-2' exhibits purple-red flower stalks.
3. *Gaura* 'SME-2' exhibits green and purple-red foliage.
4. *Gaura* 'SME-2' is propagated using vegetative stem cuttings.
5. *Gaura* 'SME-2' exhibits rose-pink flowers.
6. *Gaura* 'SME-2' is hardy in USDA Zones 6–10.
7. *Gaura* 'SME-2' is 65 cm. in height and up to 100 cm. in width at five months of age.

BRIEF DESCRIPTION OF THE DRAWINGS

The accompanying color drawings illustrate the overall appearance of the new *Gaura* cultivar 'SME-2' showing the colors as true as it is reasonably possible to obtain in colored reproductions of this type. Colors in the drawings may differ from the color values cited in the detailed botanical description, which accurately describe the actual colors of the new variety 'SME-2'.

The drawing labeled as FIG. 1 illustrates a mature one year old plant planted out-of-doors in Wonga Park, Victoria, Australia with approximate height 65 cm and approximate width 100 cm.

Figure 1:
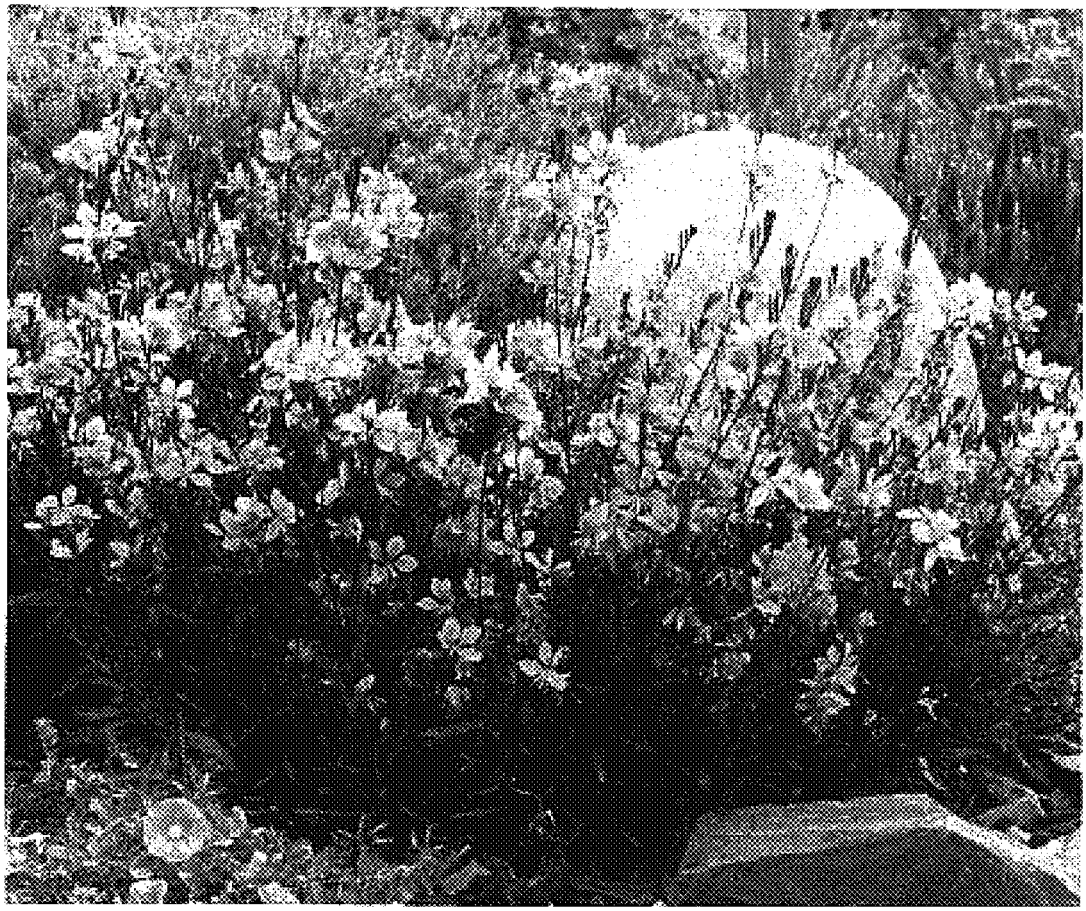
Figure 2:
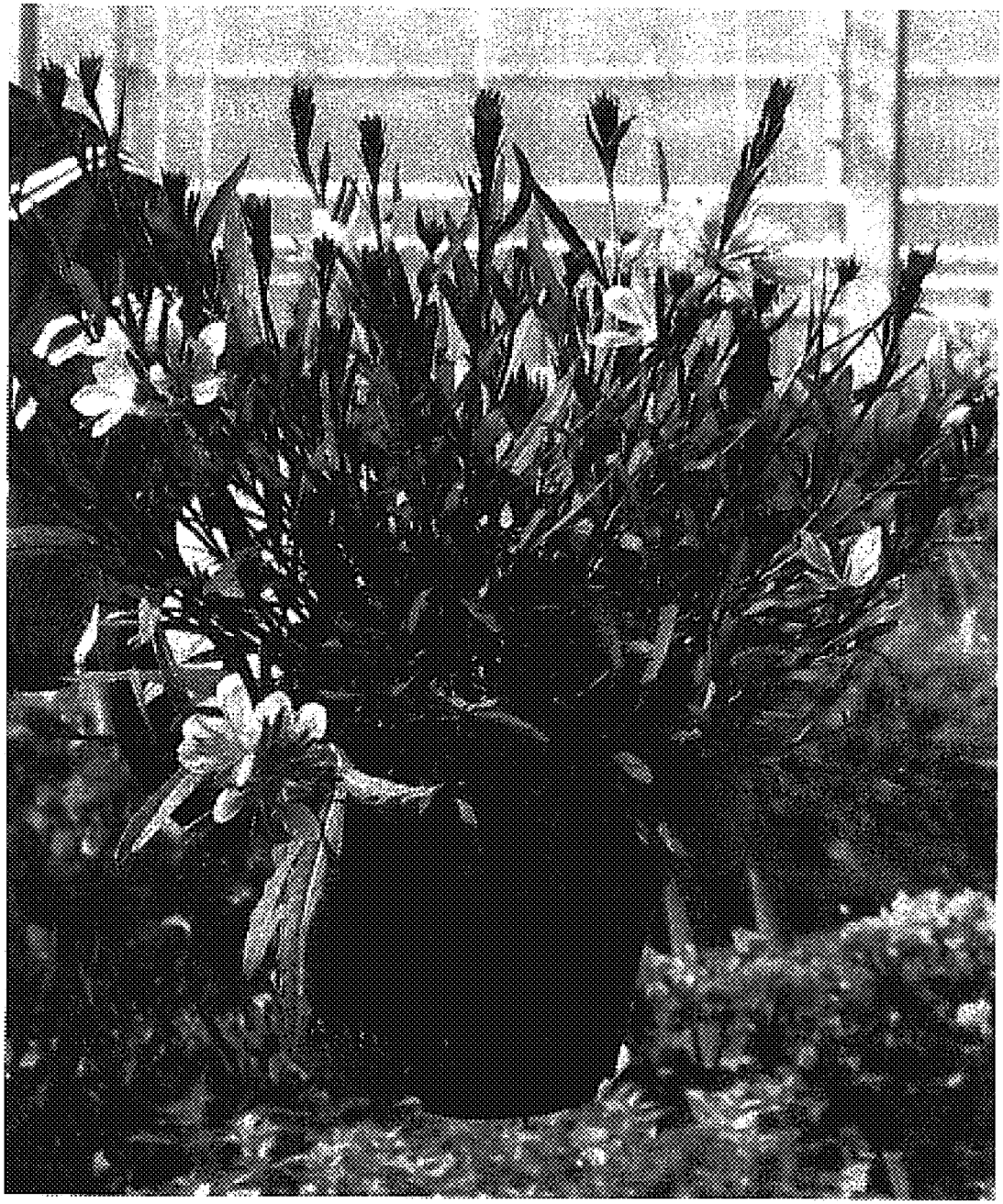

The drawing labeled as FIG. 2 illustrates a five months old plant of 'SME-2' that has been grown in a cool greenhouse in a 14 cm container and is ready for market in bud and first flower.

Figure 3:
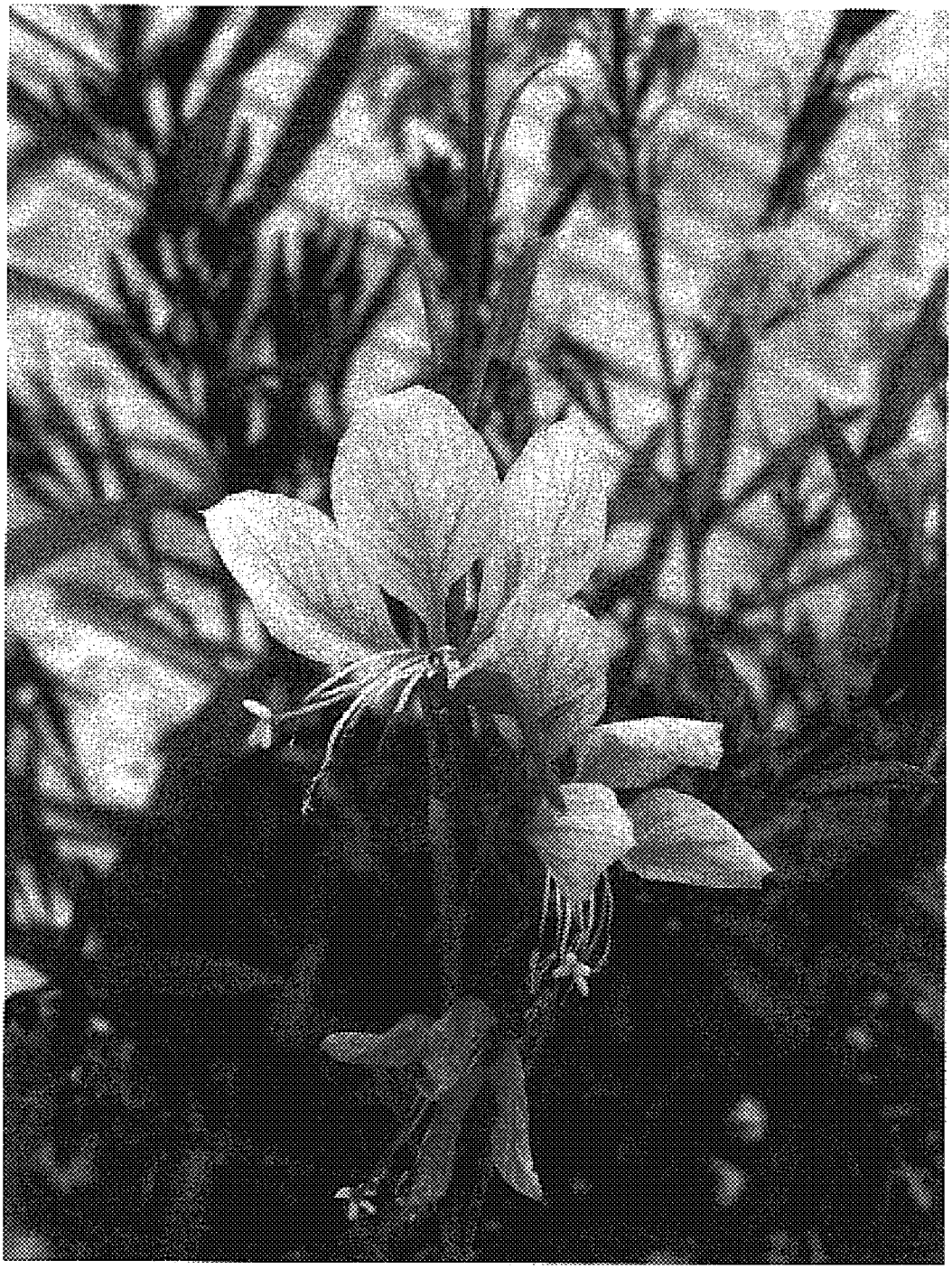

The drawing labeled as FIG. 3 presents a close-up view of a flower of 'SME-2'.

Drawings were made using conventional techniques and although colors may appear different from actual colors due to light reflectance they are as accurate as possible by conventional photography.

BOTANICAL DESCRIPTION OF THE PLANT

The following is a detailed description of the new *Gaura* plant named 'SME-2'. Data was collected in Arroyo Grande, Calif. from plants that had been received from the inventor as cuttings in early spring 2004. The plants, which grow very rapidly, were rooted and grown out of doors in one-liter containers and then transplanted into the ground. The plants were approximately five months old at the time of data collection. The color determinations are in accordance with the 2001 edition of The Royal Horticultural Society Colour Chart, except where general color terms of ordinary dictionary significance are used. The growing requirements are similar to other *Gaura*.

Botanical classification: Genus: *Gaura*.
Species: *lindheimeri*.
Denomination: 'SME-2'.
Commercial classification: Perennial.
Common name: Butterfly bush.
Use: Ornamental for container or landscape.
Cultural requirements: Plant in well-drained moderately fertile soil in full sun.
Pests and disease: No susceptibility or resistance to pests or disease are known to the inventor.
Root system: Deep rooting makes the plant very drought tolerant.
Parentage: *Gaura* 'SME-2' was selected as a single seedling grown from seed collected from a plant which was discovered within a crop of *Gaura lindheimeri* 'Passionate Pink'.
Plant description:
- *Bloom period.*—Late spring to fall.
- *Plant habit.*—Dense, upright growth habit.
- *Plant height.*—65 cm. in height after one year.
- *Plant width.*—100 cm. in width after one year.
- *Plant hardiness.*—USDA Zones 6–10.
- *Propagation.*—Propagation is accomplished using vegetative stem cuttings.
- *Time to develop roots.*—2–3 weeks are needed for initial cuttings to develop roots.
- *Crop time.*—4 months are needed to produce a finished 1-liter container.

Stem:
- *Main trunk dimensions.*—20 cm. in length and 0.50 cm. in diameter.
- *Main trunk color.*—199B.
- *Main trunk shape.*—Subcylindric.
- *Main trunk texture.*—Rigid.
- *Main trunk surface.*—Scarious.
- *Stem shape.*—Cylindrical.
- *Stem color.*—147B.
- *Stem texture.*—Flexible.
- *Stem dimensions.*—11 cm. in length and 0.25 cm. in diameter.
- *Stem surface.*—Mostly glabrous, with only a few hairs.
- *Internode length.*—Average internode length is 6.1 mm.
- *Branching habit.*—Sympodium and densely branching from main trunk.
- *Node dimensions.*—Prominent nodes 0.50 cm. in height and 0.50 cm. in width.
- *Node color.*—147A.

Foliage:
- *Shape.*—Oblanceolate.
- *Division.*—Simple.
- *Apex.*—Acute.
- *Base.*—Attenuate.
- *Venation pattern.*—Pinnate.
- *Vein color (adaxial surfaces).*—187A.
- *Vein color (abaxial surfaces).*—187A.
- *Margins.*—Entire and slightly undulate.
- *Attachment.*—Sessile.
- *Arrangement.*—Opposite.
- *Leaf surface (adaxial and abaxial surfaces).*—Glabrous.
- *Leaf appearance.*—Matte.
- *Leaf dimensions.*—65 mm–70 mm in length and 5 mm–10 mm in width.
- *Variegation.*—Absent.
- *Leaf color (adaxial and abaxial surfaces).*—Colors 147A and 187A are both individually present on all individual leaves that are above the base of the plant.
- *Basal leaf color (abaxial and adaxial surfaces).*—On leaves that are at the base of the plant, color is 147A.
- *Anthocyanin coloration.*—Strongest on new growth.
- *Fragrance.*—None observed.

Flowers:
- *Inflorescence.*—Panicle.
- *Dimensions of inflorescence.*—5 cm. in length and 1 cm. in width.
- *Shape.*—Explanate.
- *Sexuality.*—Bisexual.
- *Flower dimensions.*—2.25 cm. in diameter and 2 cm. in length.
- *Calcar dimensions.*—12 mm. in length and 3 mm. in width.
- *Calcar color.*—184C.
- *Persistent or self-cleaning.*—Self-cleaning.
- *Aspect.*—Facing outward.
- *Bud dimensions.*—2 mm. in width and 8 mm. in length.
- *Bud shape.*—Oblong.
- *Bud color.*—187B.
- *Bud surface.*—Lanate.
- *Bract color.*—184A.
- *Bract dimensions.*—8 mm. in length and 0.20 mm. in width.
- *Bract shape.*—Linear.
- *Bract surface.*—Lanate.

*Number of bracts.*—10–15 bracts.
*Number of buds per peduncle.*—An average of 10–15 buds per peduncle.
*Bud apex.*—Rounded.
*Flower color.*—Colors 65A, 65D, 68A, and N66A are individually present on individual flower.
*Petals.*—Four in number.
*Petal color* (*adaxial and abaxial surfaces*).—Colors 65A, 68A, and N66A are individually present in individual petals.
*Petal shape.*—Ovate.
*Petal dimensions.*—14 mm. in length and 6 mm. in width.
*Vein pattern.*—Pinnate.
*Vein color* (*adaxial and abaxial surfaces*).—N66A.
*Petals fused or unfused.*—Unfused.
*Petal margin.*—Entire.
*Petal apex.*—Rounded.
*Petal surface.*—Glabrous.
*Peduncle shape.*—Cylindrical.
*Peduncle color.*—187B.
*Peduncle surface.*—Puberulent.
*Peduncle dimensions.*—10 cm. in length and 2 mm. in width.
*Flower fragrance.*—None observed.

Reproductive organs:
*Stamens.*—Eight in number.
*Stamen color.*—65A.
*Stamen dimensions.*—9 mm. in length and 0.25 mm. in diameter.
*Anther color.*—187A.
*Anther dimensions.*—2.50 mm. in length and 0.50 mm. in width.
*Quantity of pollen.*—Small amount.
*Color of pollen.*—155C.
*Pistil.*—One in number.
*Pistil dimensions.*—12 mm. in length and 0.50 mm. in width.
*Pistil color.*—184D.
*Pistil shape.*—Filament.
*Style color.*—184D.
*Stigma shape.*—Four lobed.
*Stigma color.*—184C.
*Stigma dimensions.*—2 mm. in height and 2 mm. in width.
*Ovary position.*—Inferior.
*Ovary color.*—139A.
*Ovary shape.*—Globular.
*Ovary dimensions.*—3 mm. in length and 3 mm. in diameter.

Seed production: No seed production has been observed to date.

What is claimed:

1. A new and distinct cultivar of *Gaura* plant named ‘SME-2’ as described and illustrated herein.

* * * * *